United States Patent [19]

Tanaka et al.

[11] Patent Number: 5,071,705
[45] Date of Patent: Dec. 10, 1991

[54] COMPOSITE FIBRES, WATER-ABSORBING MATERIAL USING THE COMPOSITE FIBRES AS A BASE MATERIAL AND METHOD FOR PRODUCING THE SAME

[75] Inventors: Toyoaki Tanaka; Akira Nakamura; Yoshisuke Kamei; Akihiro Hashimoto, all of Kawasaki, Japan

[73] Assignee: Showa Denko K.K., Japan

[21] Appl. No.: 68,039

[22] Filed: Jun. 29, 1987

[30] Foreign Application Priority Data

Nov. 1, 1985 [JP] Japan ............................ 60-243863
Dec. 18, 1985 [JP] Japan ............................ 60-282986

[51] Int. Cl.⁵ ............................................. D02G 3/00
[52] U.S. Cl. .................................. 428/370; 57/907;
156/180; 264/147; 428/357; 428/359; 428/362;
428/364; 428/369; 428/373; 428/374; 428/221;
428/224; 428/247
[58] Field of Search ................ 428/373, 374, 375, 394,
428/395, 369, 370, 357, 359, 362, 247; 264/147;
57/907; 156/180

[56] References Cited

U.S. PATENT DOCUMENTS

| | | | |
|---|---|---|---|
| 2,772,994 | 12/1956 | Lacy | 57/260 |
| 3,460,337 | 8/1969 | Feild | 57/260 |
| 3,470,595 | 10/1969 | Goppel | 264/147 X |
| 3,503,106 | 3/1970 | Port et al. | 57/907 X |
| 3,582,418 | 6/1971 | Schuur | 264/147 X |
| 3,594,459 | 7/1971 | Keuchel | 57/907 X |
| 3,608,298 | 9/1971 | Schoots | 428/372 X |
| 3,639,573 | 2/1972 | Port | 264/147 X |
| 3,788,922 | 1/1974 | Rasmussen | 264/171 X |
| 3,914,365 | 10/1975 | Kim | 264/147 |
| 4,600,643 | 7/1986 | Dwulet | 57/907 X |

FOREIGN PATENT DOCUMENTS 0133448 1/1979 Fed. Rep. of Germany ........ 57/260
53-49902 11/1978 Japan.

Primary Examiner—Lorraine T. Kendell
Attorney, Agent, or Firm—Ostrolenk, Faber, Gerb & Soffen

[57] ABSTRACT

The present invention uses, as a base material, a multi-layer film comprising more than two layers and formed from thermoplastic resins different in melting point from one another. A sectional construction of the multi-layer film or a tape obtained from the multi-layer film is applied to a sectional construction of a fibre without modification, the multi-layer film or tape being formed into the fibre. The invention provides a composite fibre which is much more excellent as compared to a conventional heat adhesive composite fibre by melt spinning, a water-absorbing material using the composite fibre as a base material and a method for the production of the same by the stated simple means.

8 Claims, 2 Drawing Sheets ical field

The present invention relates to composite fibres in which a plurality of thermoplastic resins are integrated, a water-absorbing material obtained by adding a water-absorbing material to said composite fibres, and a method for producing them.

BACKGROUND OF ART

A composite fibre has been known as a conjugate fibre formed by simultaneously extruding two kinds of spinning solutions from a singe spinning nozzle having a partition provided therein to provide a spinning, and laminating together two kinds of fibres to form a single fibre.

Also has been known a melt composite spinning formed by using two kinds of thermoplastic resins different in a melting point from each other, for example, crystalline polypropylene (m.p. 165° C.) as a high melting point polymer and polyethylene (m.p. 125° C.) as a low melting point polymer, and simultaneously extruding both the resins in their melted state from a single spinning nozzle to form a single fibre.

In these conventional composite fibres, a spinning nozzle is used to effect spinning, and therefore, composite fibres obtained therefrom are limited to those of two component systems, and it has been extremely difficult to obtain composite fibres above three component systems.

Moreover, in the aforementioned melt composite spinning, two kinds of polymers are made into a composite form in the state of a concentric circle or an eccentric circle, and in the case where they are made into a composite form with a low melting point polymer positioned externally and a high melting point polymer, the low melting point polymer is melted so that fibres may be thermally bonded with each other. For example, after a web has been formed, the low melting point polymer is melted but when the high melting point polymer is subjected to heat treatment at a temperature at which it is not melted, contact parts of the fibres become fused, resulting in non-woven fabrics or the like. This non-woven fabric eliminates the necessity of a binder such as a synthetic rubber emulsion, and therefore has an advantage that various disadvantages caused by the use of the binder may be avoided.

However, in the above-described melt composite spinning, dies, nozzles and the like are complicated in construction, and for this reason, the composite fibres above three component systems may not only be obtained but thermo-plastic resins used therefore are limited to polymers which can be thermally welded with each other.

Furthermore, even in the composite fibres comprising two component systems, since it is difficult to change color of raw material, a colored non-woven fabric as a final product is hard to obtain. Despite the possession of characteristic of thermal adhesion, the range of utilization thereof has been greatly limited.

A problem encountered in the conventional composite fibres lies in carrying out the composition of fibres at the time of spinning. From a viewpoint that the aforesaid problem is solved if the composition is carried out by other means, the present inventors have repeatedly studided on the composition of fibres by means other than spinning.

DISCLOSURE OF THE INVENTION

Laminates having a plurality of different thermo-plastic resins laminated, for example, such as multi-layer films, tapes, sheets, etc. are well known. Such laminates (hereinafter referred to as multi-layer films) have merits that they can be molded in two layers and in three layers or more by use of various molding means such as calender method, extrusion method, casting method and the like, and materials may he colored. Furthermore, since lamination may be easily achieved through an adhesive layer, polymers which are hard to be fused together may be integrated.

Paying attention to the merits of such multi-layer films as noted above, the present inventors have made a development on composite fibres using a multi-layer film as a base material. The present inventors have found as the result of their development that the composite fibre using a multi-layer film as a base material is superior in many points to a composite fibre made by spinning and can be used in combination with a material having a water-absorbing property.

It is therefore a primary object of the present invention to provide a novel composite fibre using a multi-layer film as a base material in which thermoplastic resins above three component systems may be made into a composite form, coloring may be achieved easily, and fibres may be thermally fused together.

It is a second object of the present invention to provide a water-absorbing material comprising a composite fibre using a multi-layer film as a base material and a material having a water-absorbing property.

It is a third object of the present invention to provide a method of producing said composite fibre and said water-absorbing material.

The composite fibre according to the present invention that may achieve the aforesaid objects uses, as a base material, at least more than two multi-layer films formed from thermoplastic resins having different melting points, and they are formed into fibres by a split after said base material has been stretched, said fibre having the same section as that of the base material.

The water-absorbing material is composed of a blend of a short fibre of said composite fibre and a pulp, and a water-absorbing material as a water-proof coating is formed by fusing a high-molecular water-absorbing agent into a split yarn of the composite fibre.

The multi-layer film serving as a base material of the composite fibre according to the present invention may be manufactured by various molding methods such as a calender method, an extrusion method and a casting method, and especially an extrusion method by way of an inflation method and a T-die method is preferred.

The thermoplastic resin is preferably the resin from which a film may be molded, and a thickness thereof is not particularly limited but preferably in the range of 30 to 100 μ.

Specific examples of the thermoplastic resin are alpha olefin copolymer such as polyethylene, polypropylene, etc., polyamide, polyester, etc.

Such resins can be of a copolymer with a monomer of different kind, and can contain therein, as needed, an anti-oxidant, a lubricant, a ultraviolet absorbent, a delusterant, a stabilizer, a fire retardant, etc.

Particularly, a color film is obtained by adding a colorant, and the composite fibre of the present invention may be colored as will be described hereinafter, and a composite fibre rich in variety of color may be obtained.

A plurality of resins used in the composite fibre according to the present invention are determined according to uses of the composite fiber, but they should be different in melting point from one another because a heat fusion property must be imparted thereto. In case of three layers, it is necessary so that a resin having a low melting point is positioned externally.

A difference in melting point between a thermo-plastic resin having a low melting point and a thermoplastic resin having a high melting point is preferably that if the melting point of the former resin is Mp °C., then that of the latter resin is Mp + 10° C. or over in consideration of the heat treating conditions, extrusion conditions of a multi-layer film, stretching conditions in a post process and the like, which will be described later.

As for one example, polyethylene (m.p. 125° C.) as a thermoplastic resin having a low melting point and crystalline polypropylene (m.p. 165 ° C.) as a thermoplastic resin having a high melting point are used.

In the case where, as in the use of linear low-density polyethylene for a thermoplastic resin having a low melting point and the use of polyamide for a thermoplastic resin having a high melting point, both resins cannot be fused, an adhesive resin may be interposed between these resins for composition.

As an example, this adhesive resin used comprises a resin composition in which polyethylene or polypropylene is denatured by acid anhydride such as anhydrous maleic acid and acids. Specifically, anhydrous maleic acid denatured linear low-density polyethylene is preferred.

It is of course that the composite fiber of the present invention can be not only two and three-layer constructions but also four-layer or more, in which case, a multi-layer film is constituted in consideration of the heat treating conditions at a temperature at which the low melting point polymer is melted but the high melting point polymer is not melted.

In forming a multi-layer film according to the present invention by way of a T-die method or the like, a die lip construction may be formed into a flat type but when a ribbed die is used, a film surface is formed into an uneven surface, which remains on the surface of each fibre even after being formed into a fibre, to bring forth a drape or volume in the composite fibre.

The multi-layer film is stretched before being formed into a fibre. This stretching increases the strength of the composite fibre.

Stretching of the multi-layer film is carried out by any of stretching means such as a hot plate, a hot roll, an oven, etc. A stretching temperature and a stretching magnification are not particularly restricted but may be set to optimum conditions according to the composition and shape of the multi-layer film. However, the strength, drape and volume feeling of webs or non-woven fabrics obtained through posterior processes largely depend upon properties of the composite fibres.

Preferable examples of the stretching temperature and stretching magnification are given: For example, in the case where a multi-layer film comprised of polyethylene and crystalline polypropylene is stretched by hot rolls after completion of slit process for longitudinally cutting it, the stretching temperature is preferably in the range of 100° C. to 130° C. and the stretching magnification preferably in the range of 4 to 10 times.

A multi-layer film is formed into a fibre by splitting the film in a longitudinal direction. This split includes a case where the entire surface of a film is completely split to form a single fibre and a case where it is discontinuously, and the fibre according to the latter case assumes a state or form (split fibre) which repeats a partial connection to provide a branch-like continuation.

A coarseness and a length of each fibre are determined according to the reed or pitch of a needle of a split roll, and their dimensions are made uneven to make the coarseness and length of the fibre uneven as the case may be.

The composite fibre resulting from a fibrous form of a multi-layer film is used in the state of a continuous fibre or as a short fibre. The length of the short fibre is preferably in the range of 50 to 100 m/m.

This short fibre may be formed into a web via preliminary splitting or via direct carding process to form a non woven fabric as well as gauze, diaper covers and carpets.

The short fibre may be blended with a pulp having a water absorbing property, and when the blend is heated, a part of the short fibre is melted and as a result, a fusion partly occurs in the blend, whereby the pulp is solidified. Also, contraction of pulp caused by absorption of moisture may also be controlled, and therefore, they can be used as an absorbing material for paper diapers and an absorbing material for toilet articles.

BRIEF DESCRIPTION OF THE DRAWINGS

The drawings show a composite fibre, a water-absorbing material using the composite fibre as a base material, and a method for producing them, according to the present invention.

THE BEST MODE FOR CARRYING OUT THE INVENTION

Figure 1:
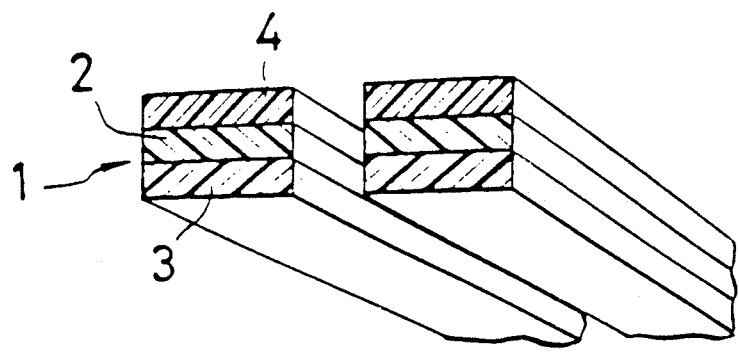
FIGS. 1 to 3 are sectional views, respectively, of a composite fibre.

As shown in the section of FIG. 1, a composite fibre 1 consists of a resin layer having a high melting point 2 and resin layers having a low melting point 3, 4 forming external layers.

Figure 2:
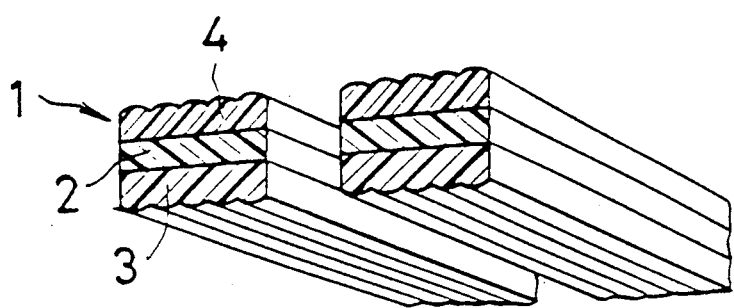
Figure 3:
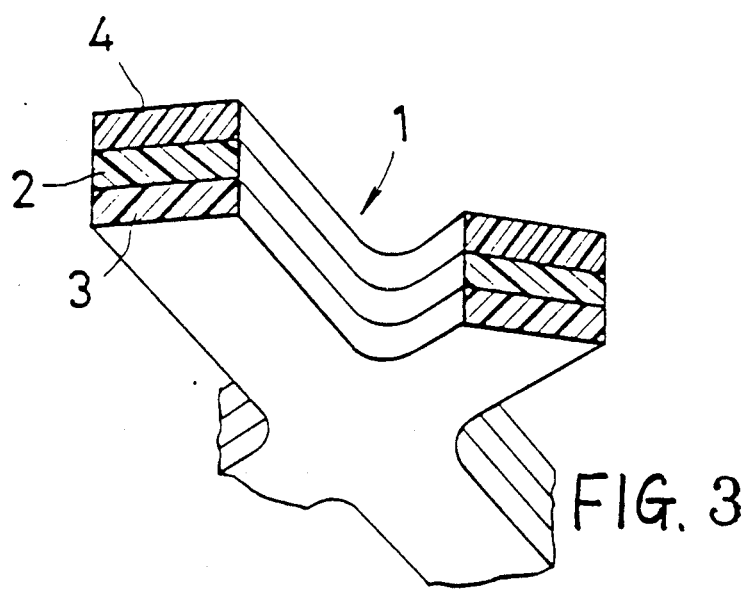

A composite fibre 1 shown in FIG. 2 has an arrangement wherein surfaces of resin layers having a low melting point, 4 are formed into uneven surfaces by use of a ribbed die. FIG. 3 shows a composite fibre 1 branched by partial connections.

Figure 4:
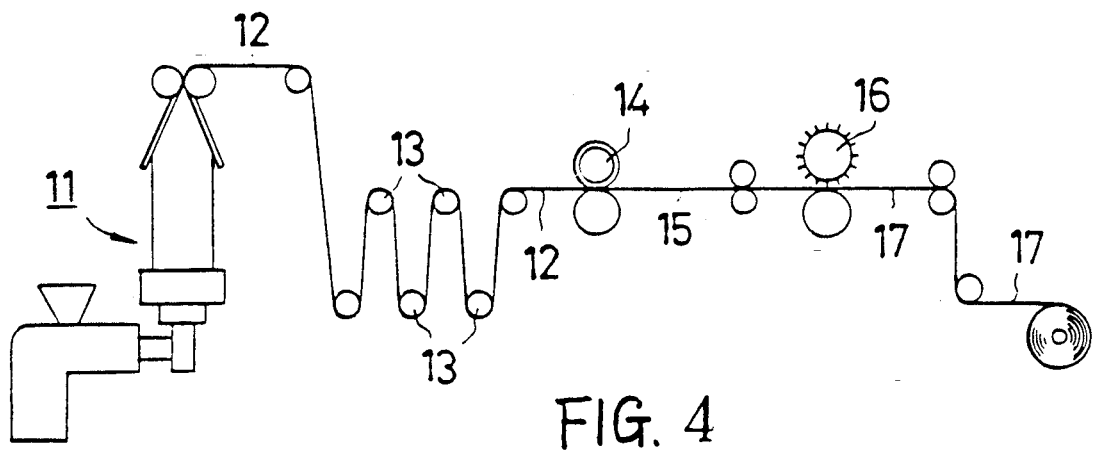
FIG. 4 is a flow chart for producing the composite fibre.

The aforesaid composite fibres 1 may be produced according to the process shown in FIG. 4.

First, a multi-layer film 12 of a three-layer construction having approximately 3μ of thickness is molded by an inflation film molding machine 11 provided with a cross head die for molding a three-layer. Subsequently, the multi-layer film 12 is passed over heated stretching rolls 13, and thereafter are slit by means of a slitter 14 into a plurality of tapes 15 having the desired width.

When this tape 15 is passed over a split roll 16 for splitting, a split yarn 17 comprised of a composite fibre having a three-layer construction is produced thereon. In this case, when each tape 15 is completely split, a single fibre as shown in FIG. 1 is produced. When a net-like fibre formed by being discontinuously split at regular intervals is untied by carding process, a branched fibre as shown in FIG. 3 is produced.

While in the aforementioned process, the multi-layer film 12 is stretched, it is to be noted that the tape 15 may be stretched.

Conditions of various parts in the aforementioned process will be given below:

| Composition of composite fibre | Example 1 | Example 2 |
|---|---|---|
| Low melting point resin layer 3 | high density polyethylene (MI = 1.0) | Linear polyethylene (MI = 1.8) |
| High melting point resin layer 2 | polypropylene (MI = 1.5) | adhesive polyolefin |
| Low melting point resin layer 4 | high density polyethylene (MI = 1.0) | nylon 6 |

Figure 5:
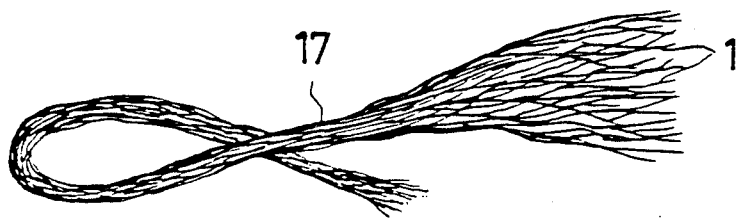
FIG. 5 is a view showing a part of split yarns in an enlarged scale.
Figure 6:
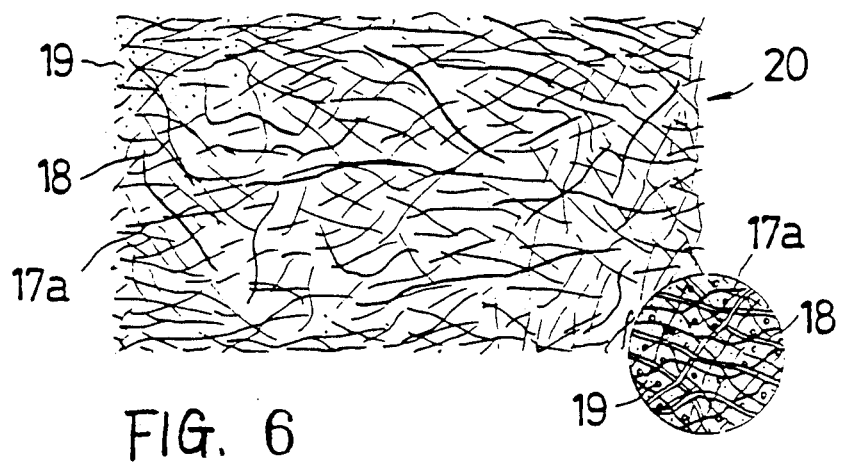
FIG. 6 is a plan view showing a water-absorbing material partly enlarged.

Conditions of extruding machines are as follows:
A. Diameter of screw: 40 mm φ (for the low melting point resin layer 3)
 Temperature of cylinder:
  C: 170° C.
  C: 230° C.
  C: 220° C.
B. Diameter of screw: 40 mm φ (for the high melting point resin layer 2)
 Temperature of cylinder:
  C: 180° C.
  C: 220° C.
  C: 230° C.
C. Diameter of screw: 32 mm φ (for the low melting point resin layer 4)
 Temperature of cylinder: Same as A above
 Die lip : 1 m/m
 Take-off speed: 10.7 m/min.
 Temperature of stretching roll: 120° C.
 Stretching magnification: 5 times
 Split: 10 d The composite fibre 1 produced under the above-described conditions takes the form of a split yarn 17 as shown in FIG. 5. This split yarn 17 is cut into short fibres in the range of 70 to 90 m/m. In case of the net-like fibre, when it is subjected to carding process, a branched fibre results. Webs which are well thermally fused are obtained from these short fibres. If approximately 2% of pigment is added to the high melting point resin layer 2, a colored thermally fused web may be obtained, the web being rich in drape and volume feeling.

To use the aforesaid composite fibre 1 as a base material for an water-absorbing material for diapers or the like, the short fibres are untied into fibres by carding process, a suitable amount of fibres 17a and fibres 18 of pulverized pulp are blended while adding thereto high molecular water absorbing agents 19 (for example, a copolymer of acrylic acid and vinyl acetate) and applying an air blow thereto, and the resulting blend is heated to a level in the vicinity of a melting point of the low melting point resins 3 and 4. It is noted that during such heating, the blend may be pressed into a flat form. Thereby, parts of the low melting point resins 3 and 4 are fused together to provide an absorbing material in which the aforesaid two fibres 17a and 18 are mixed.

The rates of the composite fibre, pulverized pulp and high-molecular water absorbing material are preferably 30%, 50% and 20%, respectively, and the amount of the composite fibre may be increased as the case may be.

INDUSTRIAL APPLICABILITY

As described above, the composite fibre according to the present invention uses a multi-layer film as a base material, the multi-layer film being split into fibres. Therefore, coloring and composition of three component systems or more which are difficult in melt composite spinning may be easily carried out, and in addition, various composite fibres different in sectional construction may be obtained by changing a shape of die and besides uses of thermally fusion composite fibres are also widely ranged.

Moreover, the composite fibres of the present invention are greatly efficacious as a base material for a water-absorbing material, particularly as a base material for a water absorbing material for toilet articles, paper diapers and the like, and therefore are extremely effective in industrial fields and widely used.

We claim:
1. Composite fibres prepared by stretching a base layer, comprising a three-layer film having an intermediate layer of a thermoplastic resin and outer layers of a thermoplastic resin comprising said three-layer film, the resin of the intermediate layer having a higher melting point than the resin of the outer layers, and then splitting said film, said fibers having the same sectional structure as in said base material.

2. Composite fibers prepared by stretching a base material, comprising a three-layer film having an intermediate layer of a thermoplastic resin and outer layers of a thermoplastic resin comprising said three-layer film, the resin of the intermediate layer having a higher melting point than the resin of the outer layers, and then discontinuously splitting said film into a net-like arrangement of fibers, said fibers having the same sectional structure as in said base material and being branched due to said splitting.

3. Composite fibers as claimed in claim 1 or 2, wherein said fibers have different lengths and different thicknesses.

4. Composite fibers as claimed in claim 1 or 2, wherein said low-melting point resin comprises high-degree polyethylene, linear polyethylene or 6-nylon, and wherein said high-melting point resin comprises polypropylene or an adhesive polyolefin.

5. Composite fibers as claimed in claim 1 or 2, wherein at least one of said layers is colored.

6. Composite fibers as claimed in claim 1 or 2, wherein the three layer film comprises a tape.

7. A method for producing a composite fibre, the method comprising slitting a three-layer film having an intermediate layer of a thermoplastic resin and outer layers of a thermoplastic resin, the resin of the intermediate layer having a higher melting point than the resin forming the outer layers, into stretched tapes having a required width, discontinuously splitting said stretched tapes by a splitting roll, and forming the resulting tapes into fibres having the same sectional construction as that of said multi-layer film.

8. A method for producing a composite fibre, the method comprising slitting a three-layer film having an intermediate layer of a thermoplastic resin and outer layers of a thermoplastic resin, the resin of the intermediate layer having a higher melting point than the resin forming the outer layers, into stretched tapes having a required width, discontinuously splitting said stretched tapes by a splitting roll, forming the resulting tapes into fibres having the same sectional construction as that of said multi-layer film, cutting said fibre into short fibres of 70 to 90 m/m, and thereafter splitting the net-like fibre into branched fibres by a carding process.

* * * * *